United States Patent
Cho et al.

(10) Patent No.: US 11,931,561 B2
(45) Date of Patent: Mar. 19, 2024

(54) BODY POSITION AND ACTIVITY BASED FLOW CONTROL FOR VENTRICULAR ASSIST DEVICE (VAD) WITH FULLY IMPLANTABLE CONTROLLER

(71) Applicant: Medtronic, Inc., Minneapolis, MN (US)

(72) Inventors: Yong K. Cho, Excelsior, MN (US); Michael F. Hess, Minneapolis, MN (US); Michael E. Eggen, Chisago City, MN (US); Michael C. Brown, Dresher, PA (US); Michael Reinert, Ramsey, MN (US)

(73) Assignee: Medtronic, Inc., Minneapolis, MN (US)

( * ) Notice: Subject to any disclaimer, the term of this patent is extended or adjusted under 35 U.S.C. 154(b) by 267 days.

(21) Appl. No.: 17/325,328

(22) Filed: May 20, 2021

(65) Prior Publication Data

US 2021/0370044 A1    Dec. 2, 2021

Related U.S. Application Data

(60) Provisional application No. 63/029,855, filed on May 26, 2020.

(51) Int. Cl.
*A61M 60/515* (2021.01)
*A61M 60/178* (2021.01)
(Continued)

(52) U.S. Cl.
CPC ........ *A61M 60/515* (2021.01); *A61M 60/178* (2021.01); *A61M 60/216* (2021.01);
(Continued)

(58) Field of Classification Search
None
See application file for complete search history.

(56) References Cited

U.S. PATENT DOCUMENTS

| 7,997,854 B2 | 8/2011 | LaRose et al. |
| 8,007,254 B2 | 8/2011 | LaRose et al. |
| (Continued) | | |

FOREIGN PATENT DOCUMENTS

| EP | 3597231 A1 | 1/2020 |
| WO | 2019210365 A1 | 11/2019 |

OTHER PUBLICATIONS

Kieran Patel, et al., Effect of Postural Changes on Cardiovascular Parameters Across Gender, Medicine, (2016) 95:28, 7 pages.
(Continued)

*Primary Examiner* — Shirley X Jian
(74) *Attorney, Agent, or Firm* — Shumaker & Sieffert, P.A.

(57) ABSTRACT

A controller for an implantable blood pump, includes an accelerometer configured to measure at least one from the group consisting of position and movement of the controller. Processing circuitry is configured to control operation of the implantable blood pump, the processing circuitry being in communication with the accelerometer, the processing circuitry being configured to adjust a speed of the implantable blood pump if the measured at least one from the group consisting of position and movement deviates from a respective predetermined threshold.

18 Claims, 5 Drawing Sheets

(51) Int. Cl.
*A61M 60/216* (2021.01)
*A61M 60/546* (2021.01)

(52) U.S. Cl.
CPC ... *A61M 60/546* (2021.01); *A61M 2205/3365* (2013.01); *A61M 2230/62* (2013.01)

(56) References Cited

U.S. PATENT DOCUMENTS

| | | | |
|---|---|---|---|
| 8,419,609 B2 | 4/2013 | Shambaugh, Jr. et al. | |
| 8,512,013 B2 | 8/2013 | LaRose et al. | |
| 9,561,313 B2 | 2/2017 | Taskin | |
| 9,616,158 B2 | 4/2017 | Yaghdjian | |
| 10,220,129 B2 | 3/2019 | Ayre et al. | |
| 11,241,570 B2* | 2/2022 | Hansen | A61M 60/216 |
| 2003/0199727 A1* | 10/2003 | Burke | A61M 60/216 600/16 |
| 2012/0004497 A1* | 1/2012 | Ayre | A61M 60/515 600/17 |
| 2012/0078031 A1* | 3/2012 | Burke | A61M 60/237 600/16 |
| 2018/0369469 A1 | 12/2018 | Le Duc De Lillers et al. | |
| 2019/0282741 A1* | 9/2019 | Franano | A61M 60/824 |
| 2019/0282745 A1* | 9/2019 | Agarwal | A61N 1/3627 |

OTHER PUBLICATIONS

Mary Anne Bassett Frey, et al., Cardiovascular Responses to Postural Changes: Differences With Age for Women and Men, J Clin Pharmacol 1994; 34:394-402, 9 pages.

International Search Report and Written Opinion dated Aug. 10, 2021, for corresponding International Application No. PCT/US2021/033810; International Filing Date: May 24, 2021 consisting of 13-pages.

* cited by examiner

BODY POSITION AND ACTIVITY BASED FLOW CONTROL FOR VENTRICULAR ASSIST DEVICE (VAD) WITH FULLY IMPLANTABLE CONTROLLER

CROSS-REFERENCE TO RELATED APPLICATION

This application claims the benefit of U.S. Application Ser. No. 63/029,855, filed May 26, 2020.

FIELD

The present technology is generally related to implantable blood pumps, and in particular, controlling a speed of the implantable blood pump based on body movement or activity level.

BACKGROUND

Implantable blood pumps are commonly used to assist the pumping action of a failing heart and typically include a housing with an inlet, an outlet, and a rotor mounted therein. The inlet may be connected to a chamber of the patient's heart, typically the left ventricle, using an inflow cannula. The outlet may be connected to an artery, such as the aorta. Rotation of the rotor drives blood from the inlet towards the outlet and thus assists blood flow from the chamber of the heart into the artery. A known type of blood pump is a ventricular assist device ("VAD") with examples including, but not limited to, the HVAD® pump and the MVAD® pump manufactured by HeartWare, Inc. in Miami Lakes, Fla., USA.

Current continuous flow pumps are capable of providing a wide range of flow rates (2-10 L/min) by programming the pump speed. However, setting the pump speed is typically done manually by selecting a speed on the programmer/monitor screen. When set, the controller maintains the speed while the actual flow and the power level change with pump's loading condition. Some VAD clinics use sophisticated methods to select the right speed setting for individual patients but others use simple methods to set the speed at implant, then potentially modify while in the hospital and before discharge. In addition, once the pump speed is set, it is rarely changed unless there are problems.

SUMMARY

The techniques of this disclosure generally relate to implantable blood pumps, and in particular, controlling a speed of the implantable blood pump based on body movement or activity level.

In one aspect, the present disclosure provides a controller for an implantable blood pump, includes an accelerometer configured to measure at least one from the group consisting of position and movement of the controller. Processing circuitry is configured to control operation of the implantable blood pump, the processing circuitry being in communication with the accelerometer, the processing circuitry being configured to adjust a speed of the implantable blood pump if the measured at least one from the group consisting of position and movement deviates from a respective predetermined threshold.

In another aspect of this embodiment, the respective predetermined threshold for the measured position is a change in position of controller from at least one from the group consisting of supine to upright and upright to supine.

In another aspect of this embodiment, the respective predetermined threshold for the measured movement is a predetermined activity level.

In another aspect of this embodiment, the processing circuitry is further configured to maintain a predetermined average flow rate if adjusting the set speed of the implantable blood pump.

In another aspect of this embodiment, adjusting the speed of the implantable blood pump includes at least one from the group consisting of increasing or reducing the set speed by a predetermined incremental amount.

In another aspect of this embodiment, the predetermined incremental amount is between 200-400 RPM.

In another aspect of this embodiment, the predetermined incremental amount is set by a clinician.

In another aspect of this embodiment, the controller is configured to adjust the speed of the implantable blood pump after a predetermined amount of time.

In another aspect of this embodiment, the controller is configured to be implanted within a patient.

In one aspect, a method of controlling an implantable blood pump includes measuring at least one from the group consisting of position and movement of a controller for the implantable blood pump. The measured at least one from the group consisting of position and movement is correlated into at least one from the group consisting of body position and activity level of a patient having the implantable blood pump. a speed of the pump is adjusted if the correlated at least one from the group consisting of body position and activity level deviates from a respective predetermined threshold.

In another aspect of this embodiment, adjusting the speed of the pump includes maintaining a predetermined average flow rate of the implantable blood pump.

In another aspect of this embodiment, the controller is implanted within a patient.

In another aspect of this embodiment, the respective predetermined threshold for the correlated body position is a change in body position from at least one from the group consisting of supine to upright and upright to supine.

In another aspect of this embodiment, the respective predetermined threshold for the correlated activity level is a predetermined activity level.

In another aspect of this embodiment, adjusting the speed of the implantable blood pump includes at least one from the group consisting of increasing or reducing the set speed by a predetermined incremental amount.

In another aspect of this embodiment, the predetermined incremental amount is between 200-400 RPM.

In another aspect of this embodiment, the predetermined incremental amount is set by a clinician.

In another aspect of this embodiment, the adjusting of the speed of the implantable blood pump occurs after a predetermined amount of time.

In another aspect of this embodiment, the predetermined amount of time is at least one minute.

In one aspect, a method of controlling an implantable blood pump includes measuring at least one from the group consisting of position and movement of a controller for the implantable blood pump. The measured at least one from the group consisting of position and movement is correlated into at least one from the group consisting of body position and activity level of a patient having the implantable blood pump. After a predetermined time delay, a speed of the pump is incrementally adjusted if the correlated at least one from the group consisting of body position and activity level deviates from a respective predetermined threshold while maintaining a predetermined average flow rate of the implantable blood pump.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
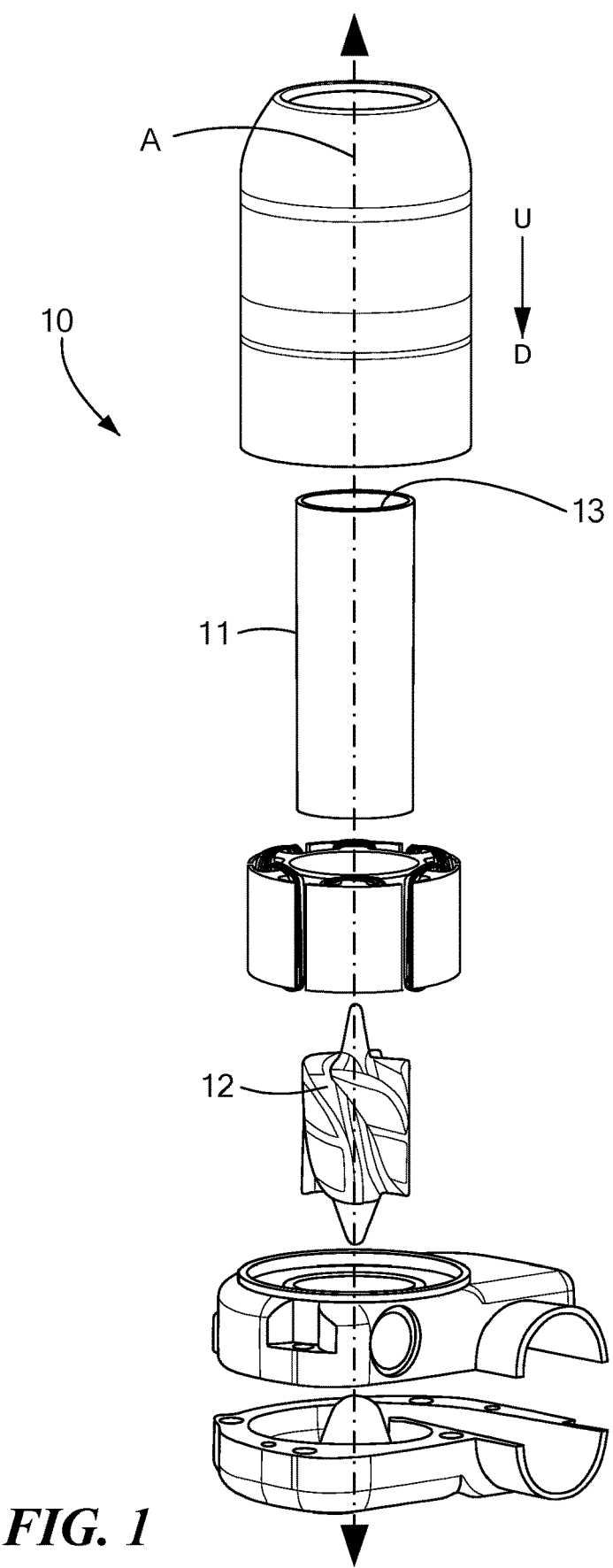
FIG. 1 is a disassembled view of an exemplary blood pump constructed in accordance with the principles of the present application.

Referring now to the drawings in which like reference designators refer to like elements there is shown in FIG. 1 a disassembled view of an exemplary implantable blood pump 10 configured to be implanted within a patient, such as a human or animal patient. The blood pump 10 may be, without limitation, the HVAD® pump or the MVAD® pump, having a movable element, such as an impeller 12 or a rotor, configured to rotate about axis "A" and impel blood from the heart to the rest of the body. The impeller 12 may rotate within a tube 11 extending from a proximal upstream end to a distal downstream end. The HVAD® Pump is further discussed in U.S. Pat. Nos. 7,997,854 and 8,512,013, the disclosures of which are incorporated herein by reference in the entirety. The MVAD® Pump is further discussed in U.S. Pat. Nos. 8,007,254, 8,419,609, and 9,561,313, the disclosures of which are incorporated herein by reference in the entirety.

Figure 2:
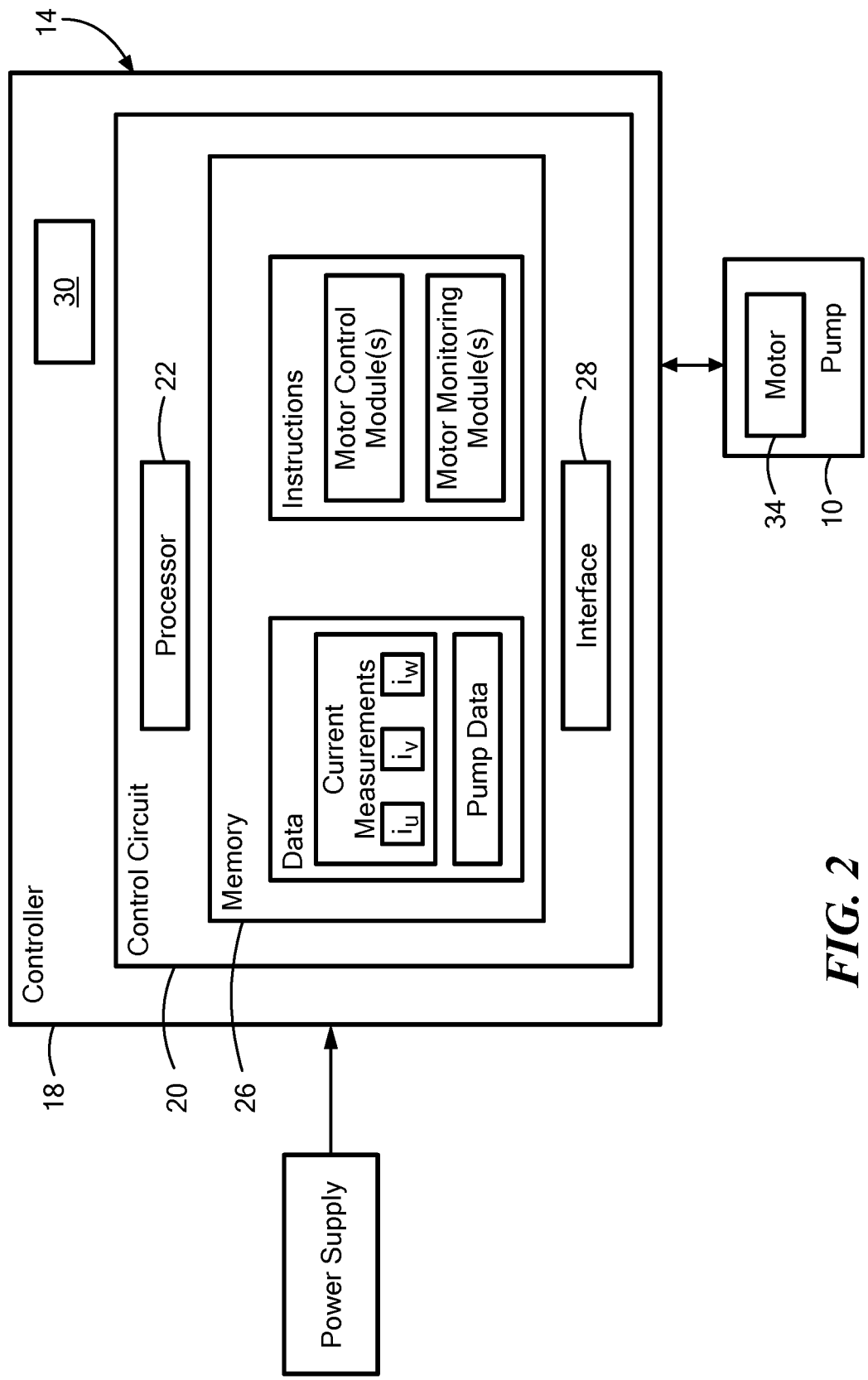
FIG. 2 is a block diagram of an exemplary system for controlling the exemplary blood pump shown in FIG. 1.

FIG. 2 is a block diagram of an exemplary system 14 for controlling a pump speed and/or other operations of the implantable blood pump 10 when the blood pump 10 is in communication with the system 14. The blood pump 10 includes a motor 16 therein and may be a separate component or form part of the system 14. In one example, the system 14 includes a controller 18 having a control circuit 20 and a processor 22 including processing circuitry 24 configured to perform the operations of the blood pump 10. The system 14 may also include a memory 26 and an interface 28, the memory 26 being configured to store information accessible by the processor 22, including instructions executable by the processing circuitry 24 and/or data that may be retrieved, manipulated or stored by the processor 22. Such instructions and/or data include that which is used to control the pump speed. In one configuration, the controller 18, which may be implanted within the patient or disposed external to the patient, includes a sensor 30 disposed within the controller 18 or remote from the controller and configured to measure a position and/or movement of the controller 18 and/or patient. For example, the sensor 30 may be a gyroscope or a 3-axis accelerometer that can measure or detect a patient's body position or activity level and communication that information to the processing circuitry 24 of the controller 18, as discussed in more detail below. In other configurations, the sensor 30 can be a wearable device worn by the patient and in communication with the controller 18. In other configurations, other sensors 30, for example, temperature sensors or transthoracic impedance sensors may be used to measure temperature and impedance of the patient and those measurements may be correlated by the controller 18 to patient movements.

Figure 3:
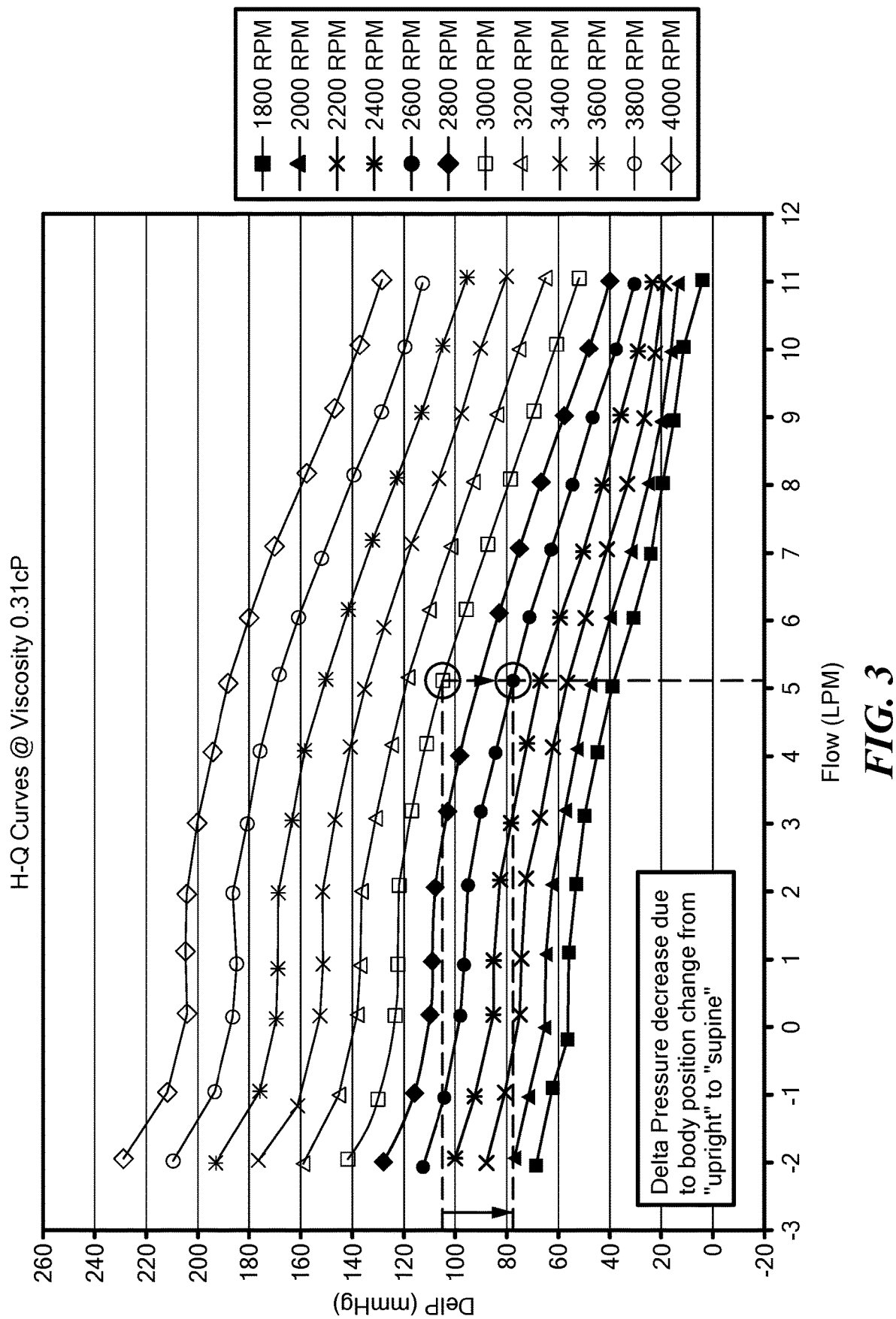
FIG. 3 is a graph showing a change in pressure on a pressure-flow curve for a given pump speed when a patient moves from upright to supine.
Figure 4:
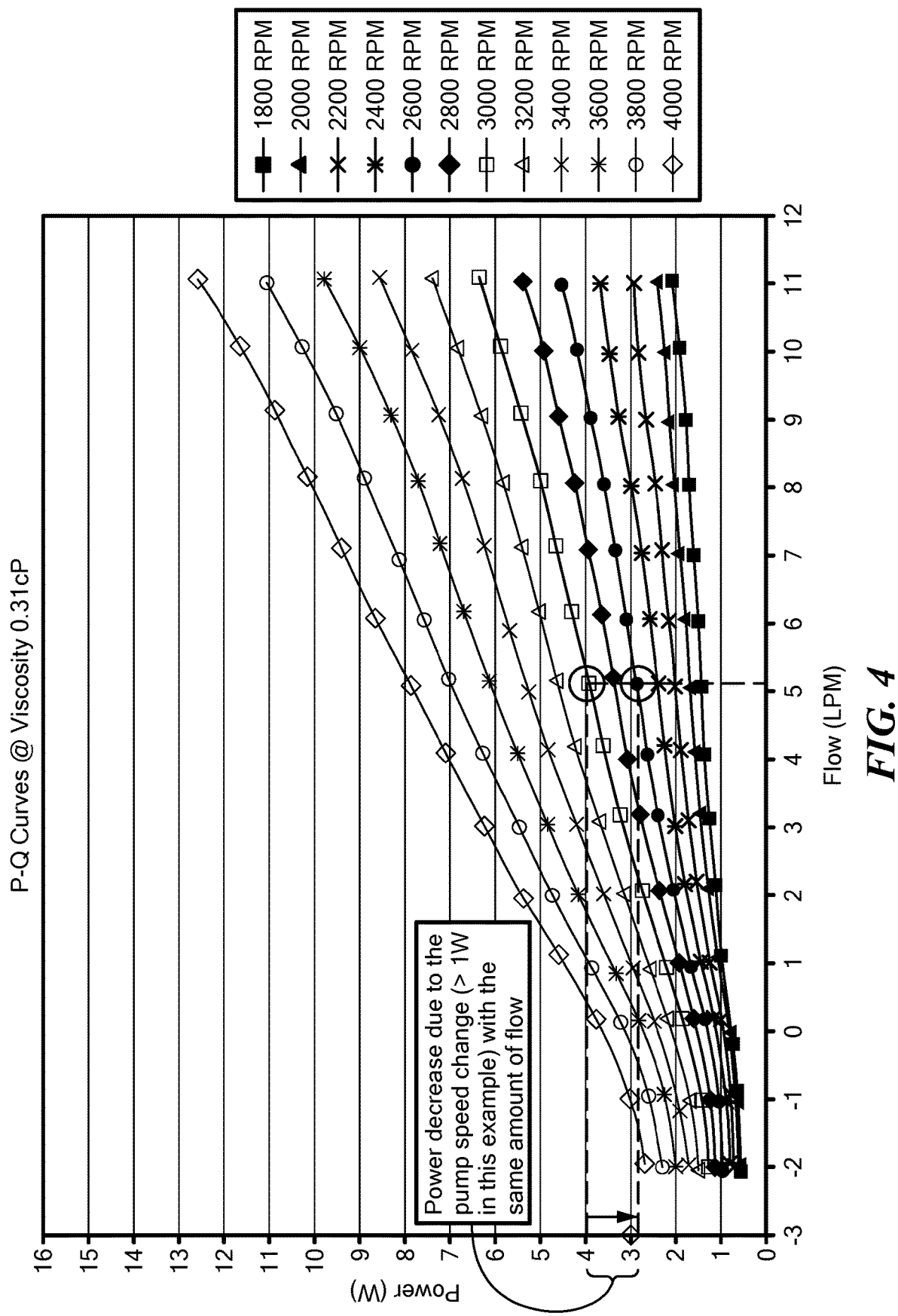
FIG. 4 is a graph showing a change in power on a power-flow curve for a given pump speed when a patient moves from upright to supine.

Referring now to FIGS. 3-4, the processing circuitry 24 of the controller 18 of the implantable blood pump 10 may be configured to automatically change a speed of the pump 10 based on at least one of the positions and movement of the controller 18. For example, the pump 10 may be programmed with a set speed, for example, 2600 RPM-3000 RPM, that operates as the base operating speed of the pump 10. In general, cardiac output is lower when standing than supine and the pump 10 may change speed based on the controller's 18 position, and therefore the patient's body position, to compensate for the hemodynamic changes due to a body position change. In particular, when a patient changes his body position from supine to standing, fluid shifts down owing to gravity, venous return decreases and initially, blood pressure decreases. To compensate, the sympathetic nervous system is activated, and peripheral vascular resistance increases and cardiac contractility as well as heart rate increases. In short, blood pressure is higher when standing than supine. In contracts when going from standing to supine, the peripheral vascular resistance decreases and cardiac preload increases owing to improved venous return. That is, when standing between 500 ml-1000 ml of blood volume drops to the lower extremities and redistributes plasma into interstitial tissues.

Continuing to refer to FIGS. 3 and 4, if the controller 18, and therefore the patient, is in the supine position, the pump pressure head becomes smaller. That is, the same average flow rate with less power can be achieved compared to the upright position. For example, as shown in FIG. 3, reducing the pump speed shifts the pressure-head to a lower RPM curve. Thus, the average flow rate is about the same owing to a change in pressure head. In this example, changing the pump's 10 speed also reduces pump power. For example, as shown in FIG. 3, when the controller 18 changes its position from upright to supine, the pressure head changes from 102 mmHg to 78 mmHg and the pump 10 speed is lower from 3000 RPM to 2600 RPM while maintain a flow rate of 5.1 L/min. Thus, the controller 18 may maintain the same average flow rate while reducing its power consumption. For example, as shown in FIG. 4, a reduction in the pump speed from 3000 RPM to 2600 RPM results in a decrease in pump 10 power from 4 W to 2.9 W while maintain the same average flow rate.

A patient's activity level may also be used to modify the pump 10 speed. Movement of the controller 18, i.e. the acceleration of the controller 18 or patient caused by movement of the patient may also trigger a change in the pump 10 speed. For example, a higher activity level over a certain activity level threshold can trigger a pump 10 speed increase. In one example, the accelerometer 30 may measure changes in acceleration of the controller 18. Repeated acceleration measurements may be indicative of a higher activity and thus cause for an increase in pump 10 speed.

Figure 5:
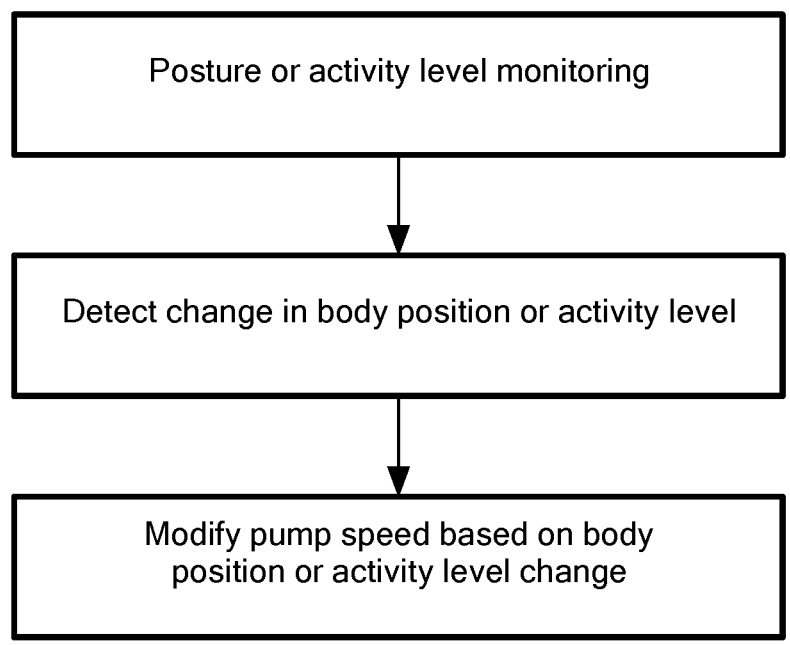
FIG. 5 is a method of operating a blood pump in accordance with the principles of the present application.

Referring now to FIG. 5, in an exemplary method of operating a blood pump, position or movement of the controller 18 of the implantable blood pump is monitored and measured. The measurements may be done with the accelerometer 30 or other sensor, such as a gyroscope, which may be calibrated before measurements are made. For example, the accelerometer 30 may calibrated to determine a starting position, for example, standing (upright) or supine. The measured position or movement may be correlated into body position and activity level of a patient having the implantable blood pump. In particular, the controller's 18 sensor 30 may be in communication the processing circuitry 24 such changes in position or movement of the controller 18 is correlated into a body position or movement which can be detected. A speed of the pump 10 may be modified or otherwise adjusted if the correlated detected body position and activity level deviate from a respective predetermined threshold. For example, if the controller 18 detects that the patient is supine and then moves to a standing position, the pump 10 may automatically increase the speed of the pump by an incremental amount, for example, between 50 to 400 RPM, which may be automatic or programmed by the clinician. That is, the controller 18 may be preset to reduce or increase a speed of the pump by, for example, 400 RPM or the clinician may program a particular speed increase or decrease. Conversely, if the controller 18 detects that the patient has moved from standing to supine, the speed of the pump may automatically decrease by the same incremental amount. Moreover, positional detection information may be integrated with other algorithms, for example, suction detection. That is, an alert associated with suction detection may be triggered earlier if combined with positional data indicating a change in position.

The controller 18 may also be configured to respond to controller 18 movements and correlate those movements its activity levels. For example, if the patient is walking or running, the sensor 30 can detect those movements and the controller 18 may increase or decrease the speed of the pump 10 accordingly by an incremental amount, for example, 200 RPM increase. That is, the controller 18 may continually increase or decrease a speed of the pump 10 depending on the duration of the movement after a time delay by the same or different incremental amount. In particular, in one configuration, the controller 18, either automatically or programmed by the clinician, is programmed with a time delay before adjusting a speed of the pump 10. For example, after a predetermined amount of time, for example, one minute or more, the pump's 10 speed may be adjusted to provide for a buffer against sudden increases or decreases in pump 10 speed. For example, a patient may be sleeping and stand up and then go back to sleep. If the totality of movements is less than the predetermined amount of time, in one configuration, no speed adjustments are made. However, if the patient is still standing after the predetermined amount of time, the speed of the pump 10 may be adjusted. Moreover, if the patient remains asleep, i.e. a longer duration supine position, the controller 18 may be configured to reduce the speed of the pump 10 as to not over load the vasculature with blood flow.

In other configurations, when sleeping for example, the controller 18 may reduce the pump 10 speed to maintain the same flow rate as standing, but may also be configured, either programmed or set by a clinician, to reduce the pump 10 speed to a predetermined flow rate during sleep that is less that the predetermined average flow rate. As such, in some instances the pump 10 speed may be reduced to maintain the same flow because of new pressure head, and use less power, but the speed may be reduced even lower as the metabolic demands during sleep are less. Moreover, during exercise, pump 10 speed may be increased, and therefore flow increased, to meet the metabolic demands of exercise.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A controller for an implantable blood pump, comprising:
 a sensor configured to measure a set of factors comprising at least one of position or movement of the controller; and
 processing circuitry configured to control operation of the implantable blood pump, the processing circuitry being in communication with the sensor, the processing circuitry being configured to:
   adjust a speed of the implantable blood pump in response to:
     an initial detection of at least one factor of the set of factors deviating from a respective predetermined threshold; and a duration of movement measured by the sensor being greater than or equal to a predetermined amount of time, wherein the duration of movement measured by the sensor coincides with or follows the initial detection.

2. The controller of claim 1, wherein the respective predetermined threshold for the position is a change in position of the controller from supine to upright or upright to supine.

3. The controller of claim 1, wherein the respective predetermined threshold for the measured movement is a predetermined activity level.

4. The controller of claim 1, wherein the processing circuitry is further configured to maintain a predetermined average flow rate in response to adjusting the speed of the implantable blood pump.

5. The controller of claim 1, wherein adjusting the speed of the implantable blood pump comprises increasing or reducing the speed by a predetermined incremental amount.

6. The controller of claim 5, wherein the predetermined incremental amount is between 50-400RPM.

7. The controller of claim 5, wherein the predetermined incremental amount is set by a clinician.

8. The controller of claim 1, wherein the controller is configured to be implanted within a patient.

9. The controller of claim 1, wherein the sensor is an accelerometer.

10. A method comprising:
  measuring, by a sensor of a controller for an implantable blood pump, a set of factors comprising at least one of position or movement of the controller; and
  adjusting, by processing circuitry of the implantable blood pump, a speed of the implantable blood pump in response to:
    an initial detection of at least one factor of the set of factors deviating from a respective predetermined threshold; and
    a duration of movement measured by the sensor being greater than or equal to a predetermined amount of time, wherein the duration of movement measured by the sensor coincides with or follows the initial detection.

11. The method of claim 10, wherein the respective predetermined threshold for the position is a change in position of the controller from supine to upright or upright to supine.

12. The method of claim 10, wherein the respective predetermined threshold for the measured movement is a predetermined activity level.

13. The method of claim 10, further comprising maintaining, by the processing circuitry, a predetermined average flow rate in response to adjusting the speed of the implantable blood pump.

14. The method of claim 10, wherein adjusting the speed of the implantable blood pump comprises increasing or reducing the speed by a predetermined incremental amount.

15. The method of claim 14, wherein the predetermined incremental amount is between 50-400RPM.

16. The method of claim 14, wherein the predetermined incremental amount is set by a clinician.

17. The method of claim 10, wherein the controller is configured to be implanted within a patient.

18. The method of claim 10, wherein the sensor is an accelerometer.

* * * * *